United States Patent [19]
Weber

[11] Patent Number: 5,686,601
[45] Date of Patent: Nov. 11, 1997

[54] DNA SEQUENCES ENCODING MUTANT ANTIVIRAL REGULATORY PROTEINS

[75] Inventor: Peter C. Weber, Canton, Mich.

[73] Assignee: The Penn State Research Foundation, University Park, Pa.

[21] Appl. No.: 18,977

[22] Filed: Feb. 18, 1993

Related U.S. Application Data

[63] Continuation-in-part of Ser. No. 726,071, Jul. 5, 1991, abandoned.

[51] Int. Cl.[6] ........ C07H 21/04

[52] U.S. Cl. ........ 536/23.72; 536/23.1

[58] Field of Search ........ 536/23.1, 23.72

[56] References Cited

PUBLICATIONS

Weber, et al., Journal of Virology, vol. 66, pp. 2261–2267 (1992).

Weber, et al., Journal of General Virology, vol. 73, pp. 2955–2961, (1992).

Perry, et al., J. Gen. Virol., vol. 67, pp. 2365–2380 (1986).

Friedman, et al., Nature, vol. 335, pp. 452–454 (1988).

*Primary Examiner*—David Guzo
*Attorney, Agent, or Firm*—Thomas J. Monahan

[57] ABSTRACT

Dominant negative or trans-dominant mutants of viral proteins represent a new and exciting means of antiviral therapy. However, the extreme specificity of a given dominant negative mutant limits its general utility in treating a broad spectrum of viral diseases, since it can typically interfere with the activity of only a single viral polypeptide encoded by a single virus. A dominant negative mutant of a gene encoding promiscuous viral transactivator protein was isolated in an attempt to generate a polypeptide which could inhibit gene expression and, therefore, virus replication nonspecifically. This mutant, a truncated derivative of the gene encoding herpes simplex virus type 1 (HSV-1) regulatory protein ICP0, was found to behave as a powerful repressor of gene expression from an assortment of HSV-1 and non-HSV-1 promoters in transient expression assays. Unexpectedly, it was also capable of inhibiting the replication of both HSV- 1 and a completely unrelated virus, human immunodeficiency virus, in cell culture. Moreover, a derivative of ICP0 with dominant mutant properties similar to that of pD19T can potentially be created by a failure to splice out the intron 2 sequences; translation of this message results in a derivative of ICP0, called ICPOR, which contains all 241 amino acids encoded by exons 1 and 2 plus an additional 21 amino acids derived from translation into the unspliced second intron. The properties of this dominant negative mutant indicate that it may be successfully utilized in treating a wide variety of different viral infections in vivo.

1 Claim, 8 Drawing Sheets

ICPO plasmids pSG424-ICPO
(aa 1 to 775)

pD19T
(aa 1 to 245)

pKST
(aa 1 to 241 + 21aa)

pHXT
(aa 1 to 105)

pHKT
(AA 1 to 212)

VP16 plasmids pVP16
(AA 1-490)

pVP16T
(AA 1-424)

FIGURE 1

Nucleotide Sequence No. 1
Exon 1 AA 1-19

```
ATG GAG CCC CGC CCC GGA GCG AGT ACC CGC CGG CCT GAG GGC   42
CGC CCC CAG CGC GAG                                        57
```

Nucleotide Sequence No. 2
Exon 2 AA 20-241

```
CCC GCC CCG GAT GTC TGG GTG TTT CCC TGC GAC CGA GAC CTG    99
CCG GAC AGC AGC GAC TCT GAG GCG GAG ACC GAA GTG GGG GGG   141
CGG GGG GAC GCC GAC CAC CAT GAC GAC GAC TCC GCC TCC GAG   183
GCG GAC AGC ACG GAC ACG GAA CTG TTC GAG ACG GGC TGC TG    225
GGG CCG CAG GGC GTG GAT GGG GGG GCG GTC TCG GGG GGG AGC   267
CCC CCC CGC GAG GAA GAC CCC GGC AGT TGC GGG GGC GCC CCC   309
CCT CGA GAG GAC GGG GGG AGC GAC GAG GGC GAC GTG TGC GCC   351
GTG TGC ACG GAT GAG ATC GCG CCC CAC CTG CGC TGC GAC ACC   393
TTC CCG TGC ATG CAC CGC TTC TGC ATC CCG TGC ATG AAA ACC   435
TGG ATG CAA TTG CGC AAC ACC TGC CCG CTG TGC AAC GCC AAG   477
CTG GTG TAC CTG ATA GTG GGC GTG ACG CCC AGC GGG TCG TTC   519
AGC ACC ATC CCG ATC GTG AAC GAC CCC CAG ACC CGC ATG GAG   561
GCC GAG GAG GCC GTC AGG GCG GGC ACG GCC GTG GAC TTT ATC   603
TGG ACG GGC AAT CAG CGG TTC GCC CCG CGG TAC CTG ACC CTG   645
GGG GGG CAC ACG GTG AGG GCC CTG TCG CCC ACC CAC CCG GAG   687
CCC ACC ACG GAC GAG GAT GAC GAC GAC CTG GAC GAC           723
```

Nucleotide Sequence No. 3
Intron 2 21 AA Encoded by this Translatable Sequence
The First TAG is the Stop Codon

```
GGT GAG GCG GGG GGC GGC AAG GAC CCT GGG GGA GGA GGA GGA   765
GGA GGG GGG GGG AGG GAG GAA TAG GCG GGC GGG CGA GGA AAG   807
```

FIGURE 2A

```
GGC GGG CCG GGG AGG GGG CGT AAC CTG ATC GCG CCC CCC GTT      849
GTC TCT TGC A                                                859
```

Nucleotide Sequence No. 4
Exon 3 AA 242-553

```
GCA GAC TAC GTA CCG CCC GCC CCC CGC CGG ACG CCC CGC GCC      901
CCC CCA CGC AGA GGC GCC GCC GCG CCC CCC GTG ACG GGC GGG      943
GCG TCT CAC GCA GCC CCC CAG CCG GCC GCG GCT CGG ACA GCG      985
CCC CCC TCG GCG CCC ATC GGG CCA CAC GGC AGC AGT AAC ACC     1027
AAC ACC ACC ACC AAC AGC AGC GGC GGC GGC GGC TCC CGC CAG     1069
TCG CGA GCC GCG GCG CCG CGG GGG GCG TCT GGC CCC TCC GGG     1111
GGG GTT GGG GTT GGG GTT GGG GTT GTT GAA GCG GAG GCG GGG     1153
CGG CCG AGG GGC CGG ACG GGC CCC TTG TC AAC AGA CCC GCC      1195
CCC CTT GCA AAC AAC AGA GAC CCC ATA GTG ATC AGC GAC TCC     1237
CCC CCG GCC TCT CCC CAC AGG CCC CCC GCG GCG CCC ATG CCA     1279
GGC TCC GCC CCC CGC CCC GGG CCC CCC GCG TCC GCG GCC GCG     1321
TCG GGA CCC GCG CGC CCC CGC GCG GCC GTG GCC CCG TGC GTG     1363
CGA GCG CCG CCT CCG GGG CCC GGC CCC CGC GCC CCG GCC CCC     1405
GGG GCG GAG CCG GCC GCC CGC CCC GCG GAC GCG CGC CGT GTG     1447
CCC CAG TCG CAC TCG TCC CTG GCT CAG GCC GCG AAC CAA GAA     1489
CAG AGT CTG TGC GGG GCG CGT GCG ACG GTG GCG CGC GGC TCG     1531
GGG GGG CCG GGC GTG GAG GGT GGG CAC GGG CCC TCC CGC GGC     1573
GCC GCC CCC TCC GGC GCC GCC CCG CTC CCC TCC GCC GCC TCT     1615
GTC GAG CAG GAG GCG GCG GTG CGT CCG AGG AAG AGG CGC GGG     1657
TCG GGC CAG GAA AAC CCC TCC CCC AGT CCA CG CGT CCC CCC      1699
CTC GCG CCG GCA GGG GCC AAG AGG GCG GCG ACG CAC CCC CCC     1741
TCC GAC TCA GGG CCG GGG GGG CGC GGC CAG GGT GGG CCC GGG     1783
ACC CCC CTG ACG                                            1795
```

DNA SEQUENCES ENCODING MUTANT ANTIVIRAL REGULATORY PROTEINS

This is a continuation-in-part of application Ser. No. 07/726,071 filed on Jul. 5, 1991, now abandoned.

BACKGROUND OF THE INVENTION

The invention herein described relates to a group of mutant regulatory proteins. These proteins exhibit generalized inhibition of gene expression and possess antiviral activity. These proteins are encoded by truncated forms of the gene coding for the HSV-1 transactivator protein ICP0. These mutants were found to be powerful repressors of gene expression from an assortment of HSV-1 and, quite unexpectedly, non-HSV-1 promoters in transient expression assays. They inhibit both HSV-1 and human immunodeficiency HIV virus in cell cultures. Therefore, unlike all dominant negative mutants of viral proteins isolated to date they can strongly inhibit the replication of several viruses, most importantly HIV virus.

By way of background, the existence of a class of mutant proteins which could exert a dominant negative effect on the activity of their wild type parents was first postulated several years ago [Herskowitz, I., Nature 329:219 (1987)]. Demonstrations that mutant viral proteins with these properties could act as antiviral agents in herpes simplex virus type 1 (HSV-1) [Friedman, A. D., et al., Nature 335:452 (1988)] and human immunodeficiency virus (HIV) [Matira, M. H., et al, Cell 58:205 (1989); Green, M., et al., ibid., p. 215] infections followed soon thereafter. Interference by such dominant negative or trans-dominant mutants can be effected by a variety of mechanisms. For example, the targeted viral protein may have to interact with a cellular protein for activity. A mutant which associates with this cellular protein in a nonfunctional manner will result in the sequestration of the essential factor from the wild type protein. This situation has been demonstrated in the HSV-1 transactivator protein VP16, which requires the host cell transcription factor OTF-1 and the promoter element TAAT-GARAT to activate immediate early viral transcription at the onset of the replication cycle. A dominant negative mutant of VP16 lacking the acidic activation domain of the wild type protein was isolated which could bind OTF-1, but did not activate transcription; this mutant was shown to inhibit virus replication by titrating out the OTF-1 required for wild type VP16 activity [Friedman, A. D., et al., Nature 335:452 (1988)].

All dominant negative mutants of viral proteins isolated to date can each interfere with the activity of only a single viral polypeptide encoded by a single virus. Thus, a mutant protein which may strongly inhibit the replication of one particular virus will have no effect on the infectious cycles of other viruses. It would, therefore, be highly desirable to create a protein which could inhibit the replication of a wide variety of viruses in a trans-dominant manner. Unexpectedly, the mutant derivatives of the HSV-1 regulatory protein ICP0 described in this work possess such an ability.

ICP0 (Infected Cell Polypeptide 0) is a 110 kd phosphoprotein which has been shown to dramatically increase gene expression from a variety of HSV-1 and non-HSV-1 promoters by a mechanism which is independent of specific promoter sequences [Everett, R. D., et al., in *Herpesvirus Transcription and Its Regulation*, E. K. Wagner (ed.), CRC Press, Boca Raton, Fla. (1991)]. It is believed that the generalized transcriptional boost which ICP0 provides may play a role in the process of HSV-1 reactivation from latent infections in vivo [Leib, D. A., et al., J. Virol. 63:759 (1989; Clements, G. B., et al., J. Gen. Virol. 70:2501 (1989); Harris, R. A., et al., J. Virol. 63:3513 (1989)]. The means by which ICP0 mediates its stimulatory effects in such a promiscuous manner are far from clear; several possibilities include interactions with the basic transcriptional machinery of the host cell, reassembly of host cell chromatin into a more activated form, or recompartmentalization of transcription complexes in the nucleus. Thus, the actual mechanism of nonspecific inhibition of gene expression by the dominant negative mutant described in this invention is not known, but it almost certainly involves nonproductive interactions with the same host cell protein(s) utilized by ICP0 during nonspecific transactivation.

The ICP0 gene encodes one of the few spliced transcripts in the HSV-1 genome; its protein-coding sequences are contained in three exons [Ferry, L. J., et al., Journal of General Virology 67:2365–2380 (1986)].

A mutational analysis of the ICP0 gene was therefore carded out in my laboratory in an attempt to map putative host cell factor interaction domains in ICP0 [Weber, P., et al., Journal of Virology 66:2261–2267 (1992); Weber, P., et al., Journal of General Virology 73:2955–2961 (1992)]. These studies resulted in the identification of the first dominant negative mutants of this regulatory protein. Further characterization of these mutants has implicated the first two exons as playing a critical role in interacting with the unknown cellular factor(s) through which ICP0 mediates transactivation.

SUMMARY OF THE INVENTION

In accordance with the present invention, dominant negative or transdominant mutants of viral proteins are presented. A truncated derivatives of the herpes simplex virus type 1 (HSV-1) regulatory protein ICP0 were isolated which generally inhibit virus replication nonspecifically. These mutants were found to be powerful repressors of gene expression from an assortment of HSV-1 and, quite unexpectedly, non-HSV-1 promoters in transient expression assays. They inhibit both HSV-1 and human immunodeficiency HIV virus in cell cultures. Therefore, tinlike all dominant negative mutants of viral proteins isolated to date they can interfere with the activity of several viral polypeptides and may strongly inhibit the replication of several viruses, most importantly HIV virus.

These dominant negative mutants may be utilized to treat a wide variety of viral infections.

Furthermore, it is possible to create a hypothetically naturally-occurring inhibitory protein with properties similar to the dominant negative mutants by alternate splicing of the ICP0 primary mRNA. This would entail a failure to splice out intron 2 from the ICP0 primary mRNA, and would result in the synthesis of a 262 amino acid protein by fusing coding sequences in exon 2 with those derived from the unspliced intron 2. A gene encoding this protein (262 amino acid) was prepared and was found to inhibit ICP0 transactivation (Table 2). These results indicate that this protein has dominant-negative phenotypic properties. A failure to inhibit intron 2 splicing and therefore drive the synthesis of this protein could be readily accomplished in vivo by the use of complementary oligonucleotides which are specifically directed against the splicing signals required for intron 2 removal. Use of complimentary oligonucleotides could therefore be applied to HSV therapeutic applications. Thus, any method (such as complimentary oligonucleotides)

which can be used to prevent intron 2 splicing for the expressed purpose of driving the expression of this 262 amino acid inhibitor protein is within the scope of this invention.

OBJECTS OF THE INVENTION

An object of this invention is to develop materials and methods useful for the control of pathogenic viruses.

It is also an object of this invention to develop nucleotide sequences which inhibit a wide variety of viruses including human immunodeficiency virus HIV.

Another object of this invention is to develop nucleotide sequences encoding for mutant antiviral proteins which can be placed in appropriate plasmid vectors and employed to inhibit a wide spectrum of viruses especially HIV virus (gene therapy approach).

In accordance with the discovery of the novel ICP0R protein, it is an object of this invention to provide an effective means of inhibiting HSV-1 virus proliferation. This protein works as an repressor of the HSV-1 replication and presents a novel way of controlling infections caused by this virus.

Another object of this invention is to develop a method of directing an alternative splicing of the ICP0 protein resulting in creation of a novel protein ICP0R.

These and other objects and advantages of the invention will become readily apparent from the following description and are particularly delineated in the appended claims.

DETAILED DESCRIPTION OF THE INVENTION

ICP0 Derivatives Containing Carboxy-Terminal Truncations in Exon 3 Behave as Dominant Negative Mutants

Several of the carboxy-terminal truncation mutants were tested for their ability to interfere with the activity of the wild type ICP0 protein by cotransfecting equimolar amounts of both plasmids in transient assays. Both pD19T (AA 1–245) and pKAT (AA 1–553) were found to behave as dominant negative murals, since the transactivation level observed in cotransfection assays reflected that of the mutant protein rather than that of the wild type protein. This effect was most dramatic in the pD19T mutant (FIG. 4), which completely lacked any transactivation capability when tested by itself and which therefore behaved as a particularly powerful repressor of ICP0 activity when tested in cotransfection experiments. Similar results were obtained with other carboxy-terminal truncation mutants of pKAT. Cotransfection with equimolar levels of the wild type ICP0 plasmid or the ICP0 null mutant pHXT was found to have no inhibitory effects on ICP0 transactivation. These results demonstrate that the interference observed was a specific effect mediated by pKAT and its derivatives and was not simply due to a promoter competition phenomenon.

The pD19T construct was examined for its ability to inhibit a wide variety of HSV-1 promoters, non-HSV-1 promoters, and HSV-1 transactivator proteins in transient expression assays. In every experiment carded out to date, this mutant protein has behaved as a powerful repressor of gene expression. The transactivation capabilities of ICP0 as well as another HSV-1 regulatory protein, VP16, were reduced to below basal levels in the presence of the pD19T mutant; similarly, the high constitutive activity of the SV40 early promoter was abolished when it was cotransfected with pD19T (Table 1). Identical results were obtained using a second non-HSV-1 promoter, that of the HIV long terminal repeat region, as well as a third HSV-1 transactivator protein, ICP4. pSG424-ICP0 stimulated gene activation and pHXT had no effect in all of these experiments. Thus, just as the wild type ICP0 protein behaves as a promiscuous transactivator of gene expression in transient assays, the dominant negative mutant of ICP0 in pD19T behaved as a promiscuous repressor.

Figure 6:
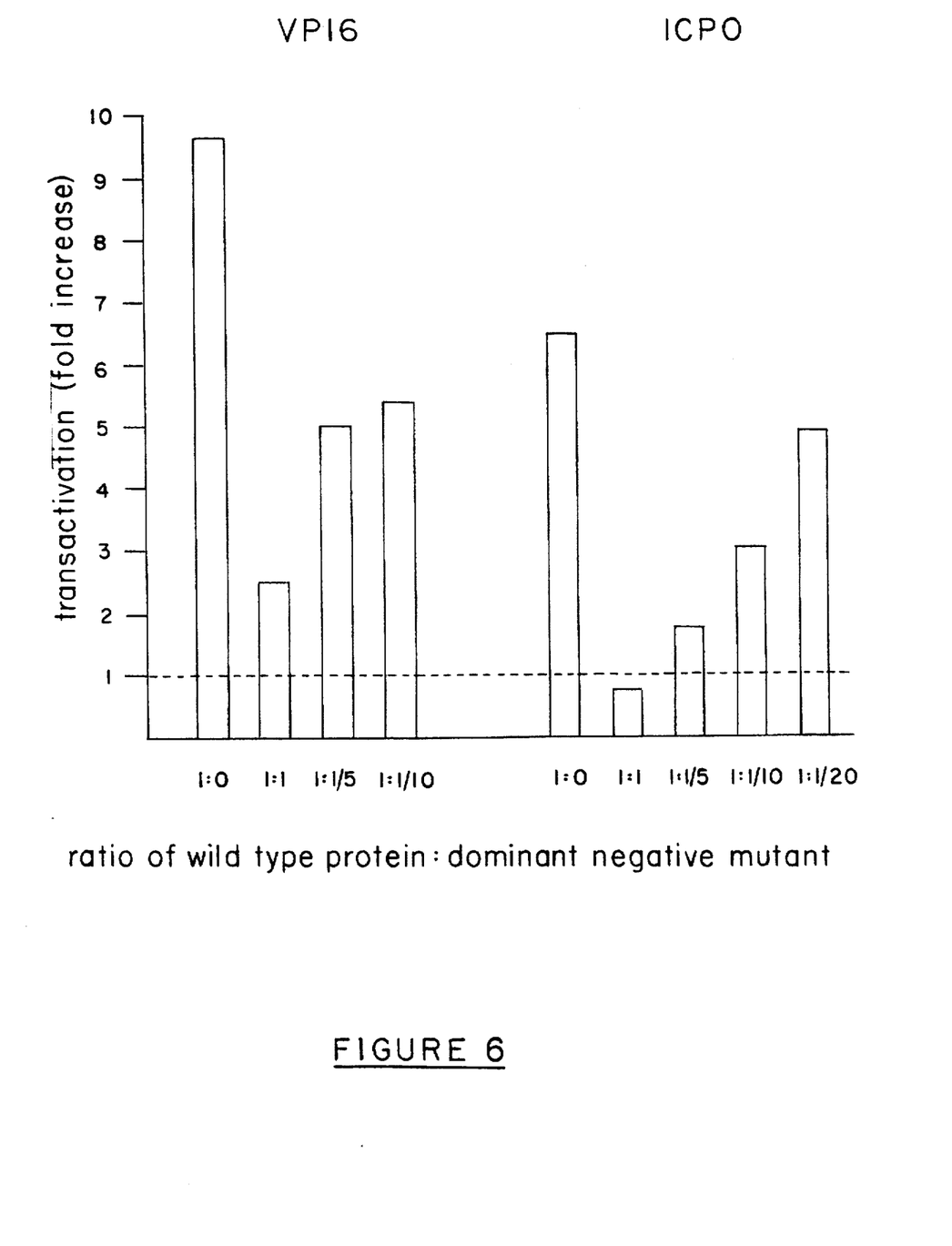
FIG. 6 is a graph comparing the strength of inhibition of gene expression by dominant negative mutants of ICP0 and VP16.

The mechanism by which the dominant negative mutants of ICP0 described in this work mediate their interference with the wild type protein is unclear. The ability of the pD19T mutant to act as a generalized suppressor of gene expression strongly suggests that ICP0 mediates its promiscuous transactivation by interacting with some very general component of the host cell transcription machinery, and that this mutant acts to effectively compete with ICP0 (and other regulatory proteins) for the binding of this factor. As proposed by others, the cellular target contacted by ICP0 could be one of the basic transcription factors which facilitates the initiation of transcription by RNA polymerase II, a component of chromatin which mediates reassembly into an activated state, or a factor involved in the recompartmentalization of transcription complexes in the nucleus. The pD 19T mutant may act to irreversibly bind up the available cellular target protein molecules to prevent interactions with ICP0 or other regulatory proteins, since effective inhibition of ICP0 transactivation is observed even at 1/20 molar concentrations of pD19T in transient expression assays (FIG. 6). Alternatively, the pD19T mutant may localize in a region of the nucleus which is distinct from that of the wild type ICP0 protein; this would act to sequester the cellular target and make it inaccessible for interactions with other proteins. These possibilities are under investigation at the present time.

Remarkably, the pD19T mutant is capable of interacting with the cellular target required for ICP0 transactivation in spite of having lost all but four amino acids of the third exon; this amounts to a deletion of over two-thirds of the wild type coding sequences. These results indicate that the domain of ICP0 which interacts with the putative cellular target for this protein is encoded by the first two exons. Not surprisingly, this region corresponds to the most mutation-sensitive region of the molecule in several mutagenesis studies. Furthermore, the ICP0 homologs found in other herpesviruses, including varicella zoster virus (VZV), pseudorabies virus, and bovine herpesvirus 4, are considerably smaller than ICP0 and shows sequence homology only to this same region. It is interesting to note that, like the pD19T mutant, the VZV ICP0 homolog manifests repression rather than transactivation characteristics in transient expression assays. These observations raise the interesting possibility that herpesviruses utilize repressor proteins as a means of downregulating gene expression during infection. Indeed, the dominant negative mutant of ICP0 encoded by pD19T has been found to behave as a powerful suppressor of HSV-1 replication. Such a repression mechanism may play an important role in the determination of host range or even in the establishment of latent infections in vivo.

Figure 1:
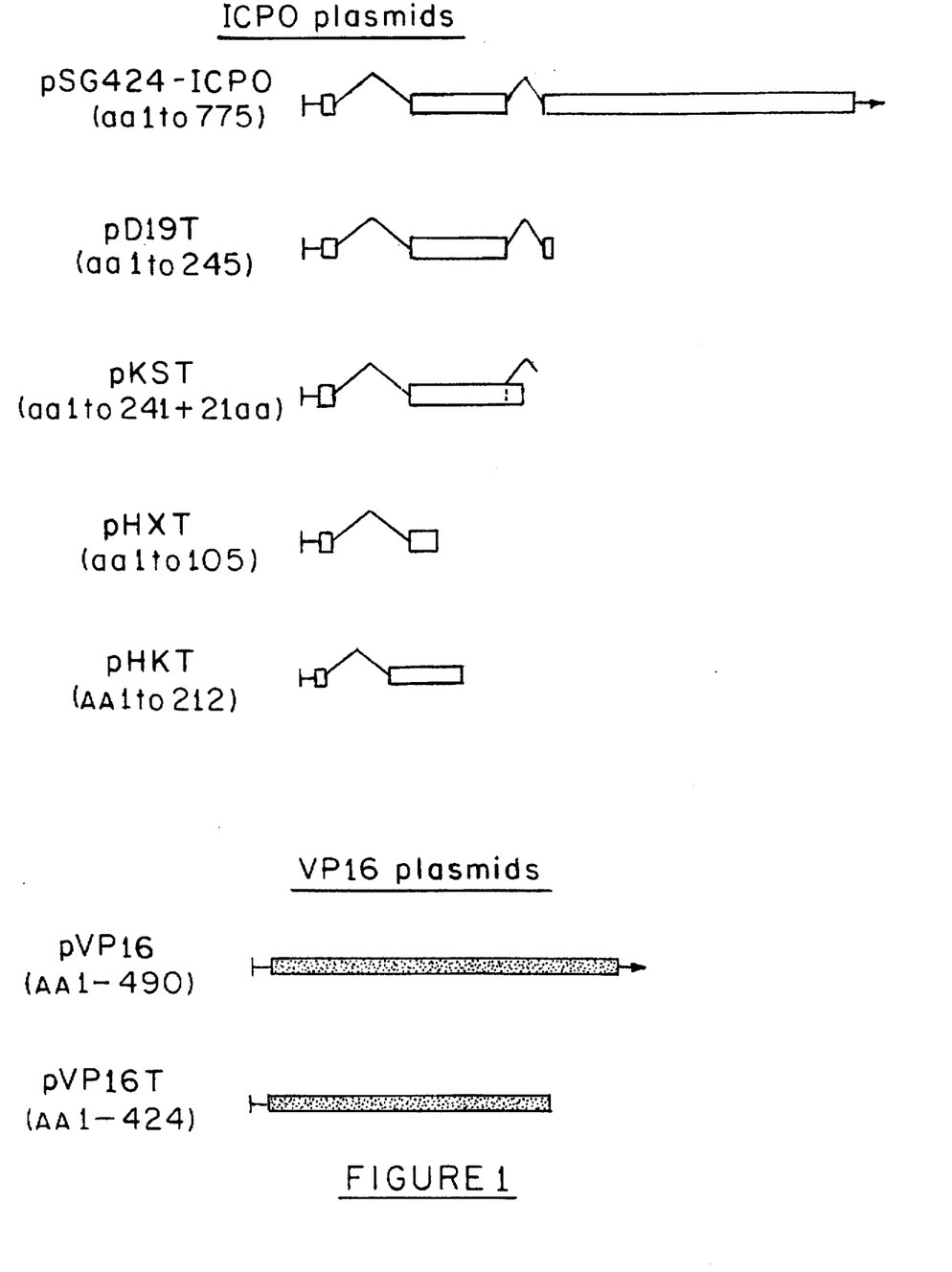
FIG. 1 presents plasmids encoding wild type and dominant negative mutants of the HSV-1 transactivator proteins ICP0 and VP16.

The proline-rich region appears to be capable of restoring some transactivation function to the domain encoded by the first two exons, but additional carboxy-terminal sequences (AA 554–775) are required for complete restoration of activity (FIG. 1). Thus, the third exon encodes a domain(s) which is essential for converting the interaction between the amino-terminal region of ICP0 and its cellular target into a transactivation phenomenon. The deletion of these sequences in pD19T therefore causes the promiscuous transactivator protein ICP0 to be convened into a promiscuous repressor. Additionally, the carboxy-terminal region of ICP0 apparently serves to alter the conformation or availability of the target binding domain encoded by the first two exons, since deletion of AA 554–775 in pKAT (and its deletion mutants) results in a derivative which can out compete the wild type ICP0 for this factor. It may be that the carboxy-terminal sequences which prevent the formation of such a high affinity interaction domain play a vital role in preventing squelching of other ongoing transcriptional processes. Studies aimed at further defining these functional domains in ICP0 are currently underway.

A Novel Protein ICP0R

The structure of the pD19T mutant suggests that only exons 1 and 2 are required for the dominant negative phenotype, since all but 4 amino acids of the third exon have been deleted in this derivative. Inspection of the ICP0 gene sequence (Perry et al. 1986) revealed that a failure to splice intron 2 from the primary ICP0 transcript would result in a truncated protein which would be structurally very similar to the pD19T mutant. This derivative would contain all 241 amino acids encoded by exons 1 and 2, plus an additional 21 amino acids derived from translation into the tinspliced second intron. To investigate the properties of this hypothetical polypeptide, a truncated ICP0 gene was constructed which expressed this protein. The ICP0 mutant contained in plasmid pKST (FIG. 1) has lost all of the exon 3 coding sequences as well as the splice acceptor site for intron 2, so that the coding sequences in intron 2 cannot be spliced out. As a restfit, pKST encodes the same 262 amino acid protein which would be generated if intron 2 was not removed from the primary ICP0 transcript. When tested in cotransfection assays with the wild type ICP0 gene, the pKST mutant was found to possess a dominant negative phenotype which was nearly identical to that of the pD19T mutant. Thus, HSV-1 can potentially encode for its own transdominant mutant of the ICP0 protein through an alternative splicing mechanism. Since this polypeptide can repress the transactivation functions of, and is partially derived from the coding sequences for ICP0, it has been given the designation ICP0R. Further studies are underway to demonstrate the existence of this protein in HSV-1-infected cells.

Delivery of the ICP0R Coding Sequences to Sites of Latent HSV-1 Infection

Recent advances in HSV-1 vector development have made it possible to deliver any gene of interest into the central nervous system. The ICP0R coding sequences can be mobilized to sites of latent infection using a modification of the defective virus approach. First, the coding sequences from pKST (encoding ICP0R) and pHXT (encoding a null mutant of ICP0 as a negative control) can be inserted downstream of the LAT promoter. This promoter can be used in expression of the proteins for two reasons: first, the LAT RNAs represent the only transcription unit which is expressed at high levels in latently infected neuronal cells; and second, the LAT promoter is only weakly expressed in productively infected tissue culture cells. The latter consideration is important since repression by ICP0R during propagation of the defective virus stocks would be highly undesirable. Since some but not all of the elements involved in high level expression from this promoter in neuronal cells have been defined, care was taken to include large stretches of sequences upstream and downstream of the start of transcription in these plasmids. Once these constructs have been generated, they can be grown as amplicon (i.e. defective virus) vectors, since they will contain an HSV-1 origin of replication and the cleavage/packaging signals. These plasmids can be cotransfected into Veto cells with infectious HSV-1 (strain KOS) DNA, and the resulting virus stocks can be propagated as amplicons by repeated serial passages at low dilution.

The amplicon stocks prepared in this fashion will have a significant population of particles which contain tandem head-to-tail-linked copies of the pKST or pHXT plasmids instead of viral genomes. These two virus stocks can be used to establish latent infections in mice by the footpad route of inoculation. Once latency has been verified in these animals, coculture of explanted dorsal root ganglia cells can be performed for the two amplicon stocks to see if elevated levels of ICP0R protein do reduce the frequency of reactivation. Additionally, experiments can be carded out in which the amplicon stocks are used to inoculate mice which are already latently infected with HSV-1 (strain 17) to see if delivery of the ICP0R coding sequences can prevent reactivation of a pre-existing latent infection. Since numerous restriction site differences occur within the genomes of strain 17 and strain KOS, which was used to generate the amplicon stocks, a simple means is available for distinguishing between the resident and supefinfecting HSV-1 strains during quantitation of reactivated virus.

This represents an approach to experimentally analyze the use of this invention in an animal model system. However, similar approaches could be applied towards treating diseases in humans.

Since dominant negative mutants of ICP0 like pD19T possess broad spectrum antiviral activity, their use need not be restricted to treating HSV-1 infections as outlined above. Other gene delivery systems such as retroviral vectors can be used to direct this mutant to cells which may be infected with a wide variety of viruses.

Figure 7:
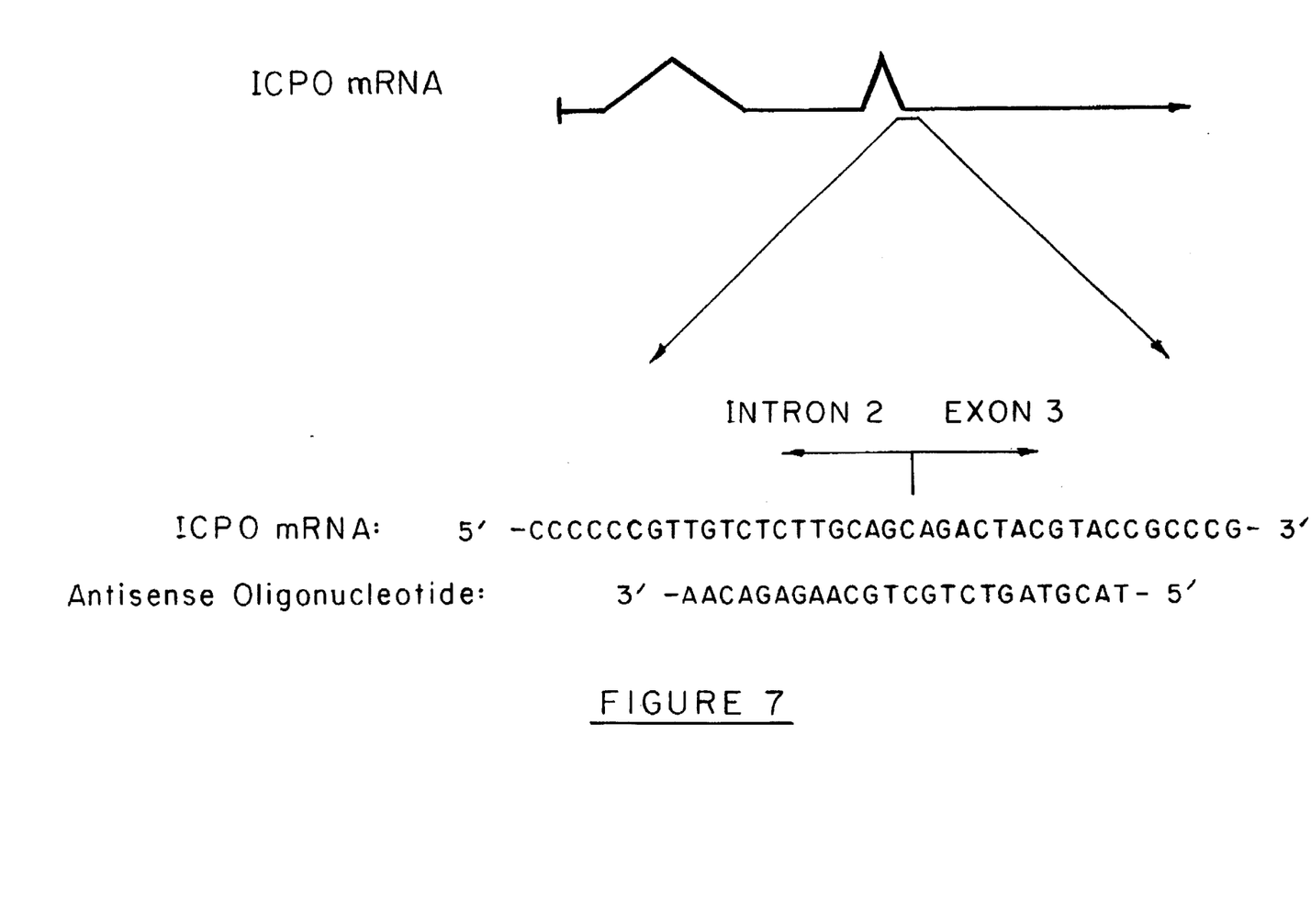
FIG. 7 presents an example of anti-sense oligonucleotide interfering with splicing signals of ICP0, SEQ ID NO: 5 and 6).

Use of Antisense Oligonucleotides to Drive Production of the ICP0R Protein in HSV-1-Infected Cells Antisense oligonucleotides have previously been used to inhibit HSV-1 replication by binding to splicing sites required for the proper processing of the ICP22 and ICP47 mRNAs. A similar antisense strategy can be employed to see if suppression of HSV-1 replication can also be induced by binding up the splice acceptor site required for intron 2 removal from the primary ICP0 transcript. The inhibition of intron 2 splicing would not only permit the production of ICP0R, but would also prevent the synthesis of ICP0; both of these events should result in the downregulation of HSV-1 gene expression. These experiments can employ a synthetic oligonucleotide which spans the splice acceptor site of the ICP0 transcript (FIG. 7, SEQ ID NO.: 5 and 6). A second oligonucleotide lacking any homology to ICP0 can be used as a negative control. Thiolate derivatives of the oligonucleotides can be synthesized since these forms are resistance to nucleases in vivo and are readily taken up by cells without the need for transfection. Note that any antisense oligonucleotide which drives ICP0R production, and not just the one shown in the figure, should be considered. Also note that other antisense approaches can be envisioned, such as delivering a gene driven by the LAT promoter which is capable of expressing an antisense RNA in neuronal cells to sites of HSV-1 infection.

The ability of this oligonucleotide to inhibit HSV-1 replication when added to the culture medium at 4 hours before, during, and 4 hours after infection can be examined. Furthermore, the ability of this reagent to drive the production of ICP0R production by inhibiting intron 2 splicing can be determined by analyzing both immediate early polypeptide synthesis in cycloheximide reversal experiments and ICP0 mRNA splicing in PCR experiments. Finally, the specificity of the oligonucleotide in inhibiting ICP0 activity can be continued by examining its ability to suppress ICP0 transactivation in transient expression assays. Since it can have a bimodal effect in inhibiting HSV-1 gene expression, this oligonucleotide may prove to be a powerful antiviral agent in the treatment of acute HSV-1 infections.

EXAMPLE 1

Mutant Derivatives of the HSV-1

Plasmids Containing Nucleotide Sequences Encoding Transactivator Proteins ICP0, VP16, and ICP0R and Other Carboxy-Terminal Truncation Mutants The most potent dominant negative mutant of ICP0 is contained in plasmid pD19T and was obtained in a mutational analysis of the wild type protein. It contains a C-terminal truncation of the ICP0 protein, so that it retains AA 1 - 245, but has lost AA 246–775 (FIG. 1). Two other plasmids containing ICP0 coding sequences were also used in the studies presented below. pSG424-ICP0 encodes all 775 amino acids of ICP0 and was used as a wild type construct. pHXT, however, encoded only AA 1–105 of ICP0 and completely lacked both the transactivation properties of the wild type protein and the repression properties of the pD19T mutant; it was employed as a negative control in all of the experiments presented.

Figures 3A, 3B:
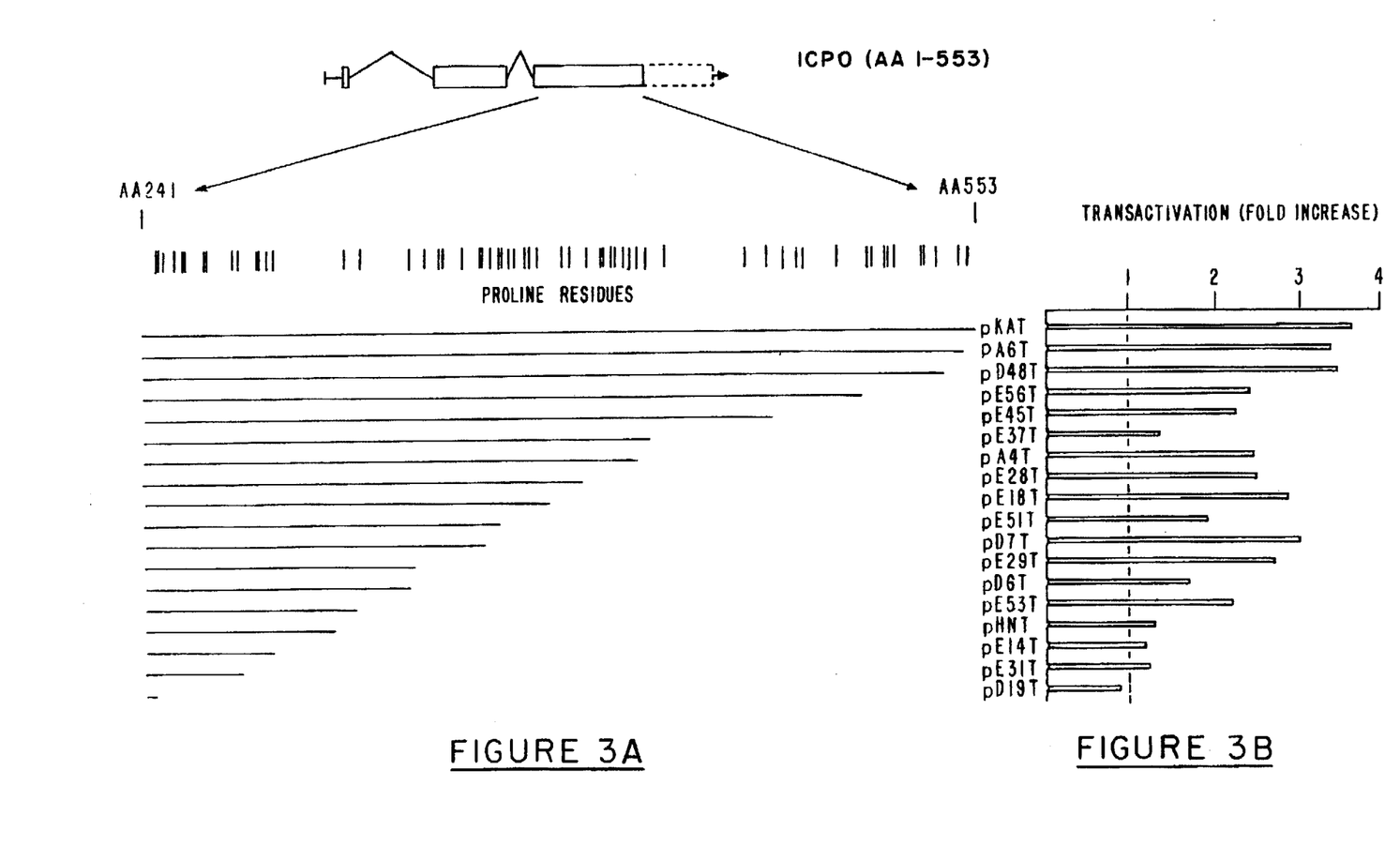
FIG. 3 (Parts A–B) shows various C-terminal truncations of ICP0 and their transactivation.

Plasmids encoding wild type and dominant negative mutant derivatives of the HSV-1 transactivator proteins ICP0 and VP16 are graphically presented in FIGS. 1 and 3. All plasmids were constructed as described below. Reporter constructs used in this work included the promoter for the HSV-1 late gene encoding glycoprotein C fused to the chloramphenicol acetyltransferase (CAT) gene (pgC-CAT); the promoter for the HSV-1 immediate early gene encoding ICP4, including a VP16-responsive TAATGARAT element, fused to the CAT gene (pTAAT-CAT); and the early promoter of SV40 fused to the CAT gene (pSV40-CAT). The construction of pgC-CAT has been described previously. pTAAT-CAT was constructed in two steps: first, the 0.2 kb SstII/BamHI fragment of pFH100 containing the ICP4 promoter was inserted into the SstII and BamHI sites of the vector sequences of pTn51sv; then, the 1.6 kb BglII/HindIII fragment of pgC-CAT containing the CAT gene was inserted into the BamHI and HindIII sites of this plasmid. pSV40-CAT was constructed in four steps: first, the GAL4 sequences of pSG424 contained in a 0.5 kb BglII/BamHI fragment were deleted out to create pSG424; next, the 1.6 kb BglII/HindIII fragment of pgC-CAT containing the CAT gene was inserted into the BamHI and HindIII sites of pUC18; the CAT gene was then transferred out of this plasmid as a 1.6 kb KpnI/HindIII fragment and inserted into the KpnI and HindIII sites of the vector pGEM7; finally, the CAT gene was placed downstream of the SV40 early promoter in pSG424 as a 1.6 kb KpnI/SstI fragment. pVP16 contains the wild type VP16 gene and was constructed by inserting the 4.2 kb BglII/PstI fragment of pSG22 into the BamHI and PstI sites of pUC19.

All carboxy-terminal truncating mutations of ICP0 were made using the vector pSG424, which contains a polylinker with numerous cloning sites, an adjacent region containing stop codons in all three reading frames that truncates any inserted protein-coding sequences, and an SV40 polyadenylation signal. pSG424-ICP0 contains all 775 amino acids of the wild type ICP0 gene and was constructed by inserting the 4.6 kb HindIII/HpaI fragment of pICA15 into the HindIII and SmaI sites of pSG424. pHKT contains amino acids 1–212 of ICP0 and was constructed by inserting the 2.3 kb HindIII/KpnI fragment of pICA15 into the HindIII and KpnI sites of pSG424. pHXT contains amino acids 1 - 105 of ICP0 and was constructed by inserting the 2.0 kb HindIII/XhoI fragment of pIGA15 into the HindIII and SalI sites of pSG424. pD48T, pE56T, pE45T, pE37T, pE28T, pE18T, pE51T, pD7T, pE29T, pD6T, pE53T, pE14T, pE31T, and pD19T contain amino acids 1–541, 1–509, 1–474, 1–428, 1–406, 1–394, 1–374, 1–370, 1–343, 1–341, 1–322, 1–290, 1–278, and 1–245 of ICP0, respectively, and were constructed by inserting the smaller of two KpnI/EcoRI fragments (ranging in size from 0.2 kb to 1.2 kb) of p110D48/1, p110E56, p110E45-1, p110E37, p110E28-1, p110E18, p110E51-1, p110D7, p110E29-1, p110D6, p110E53-1, p110E14-1, p110E31-1, and p110D19, respectively, into the KpnI and EcoRI sites of pHKT. pKAT contains amino acids 1–553 of ICP0 and was constructed in three steps: first, the vector pUC19-0.5HK was created by inserting the 0.5 kb HindIII/KpnI fragment of pSG424 into the HindIII and KpnI sites of pUG19; next, the 1.2 kb KpnI/AatII fragment of pICA15 was inserted into the KpnI and SmaI sites of pUC19-0.5HK; finally, this insert was removed as a KpnI/EcoRI fragment and placed into the KpnI and EcoRI sites of pHKT. pA6T and pA4T contain amino acids 1–549 and 1–424 of ICP0, respectively, and were constructed in two steps: first, the 1.2 kb and 0.8 kb KpnI/HindIII fragments of p110A6 and p110A4, respectively, were inserted into the KpnI and HindIII sites of the vector pGEM7; then, the inserts were removed as KpnI/SstI fragments and placed into the KpnX and SstI sites of pHKT. pHNT contains amino acids 1–312 of ICP0 and was constructed by inserting the 2.7 kb HindIII/NruI fragment of pIGA15 into the HindIII and SmaI sites of pSG424.

The novel ICP0R protein is encoded by sequences in pKST plasmid. pKST contains amino acids 1–241 of ICP0 as well as 21 amino acids derived from the beginning of the second intron of ICP0. It was constructed in two steps: first, the 0.2 kb KpnI/Sau3AI fragment of pill (Everett, 1987) was inserted into the KpnI and BamHI sites of pGEM7 (Promega); then, this insert was removed as a KpnI/SstI fragment and placed into the KpnI and SstI sites of pHKT. The Sau3AI site which serves as the end point of the 3' deletion in pKST maps 23 bp upstream of the splice acceptor site of intron 2.

pVP16T encodes amino acids 1–424 of VP16 and was constructed by inserting the 2.9 kb BglII/SstI fragment of pSG22 (Goldin et al., 1981) into the BglII and SstI sites of pSG424. This derivative has lost the powerful acidic transcriptional activation domain encoded by the last 66 amino acids of the wild type VP16 protein, enabling VP16T to possess a dominant negative phenotype analogous to that of the mutant described by Friedman et al. (1988).

In all plasmids, the coding sequences for the GAL4 gene in pSG424 were replaced by ICP0 DNA.

pSG424-ICP0 and pVP16 contain the wild type ICP0 and VP16 genes, respectively. pD19T, pHXT, and pVP16T encode truncated versions of these proteins. The structure of the plasmids is represented in FIG. 1. Open boxes represent the three protein-coding exons of ICP0; shaded boxes represent the coding sequences of VP16; and lines represent transcripts and introns.

Figure 2A:
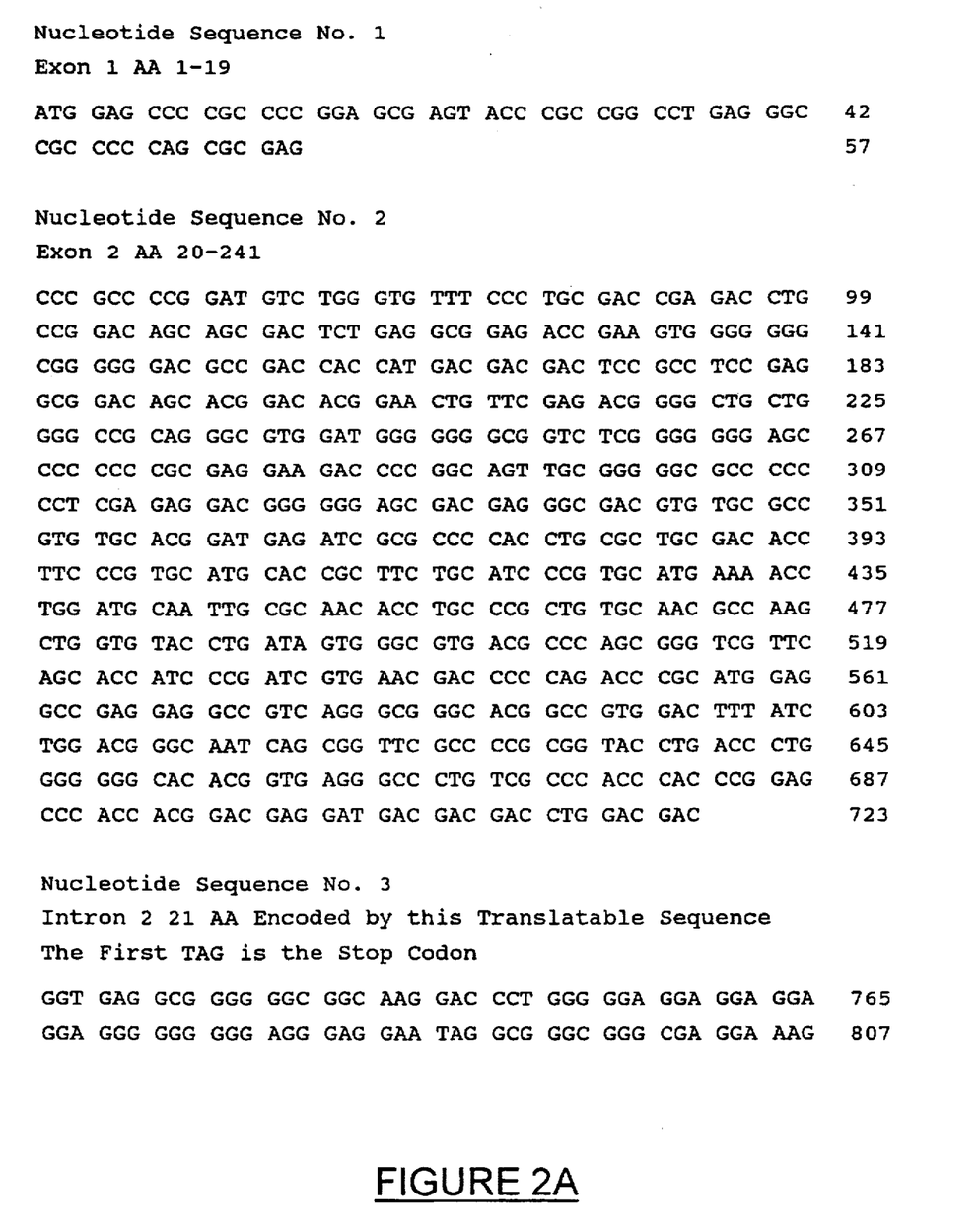
FIG. 2 (Parts A–B) presents the nucleotide sequence codings for ICP0 AA 1–553, SEQ ID NO. 1–3, and additionally nucleotide sequences from intron 2 coding for the 21 amino acids in ICP0R, SEQ ID NO. 4.
Figure 2B:
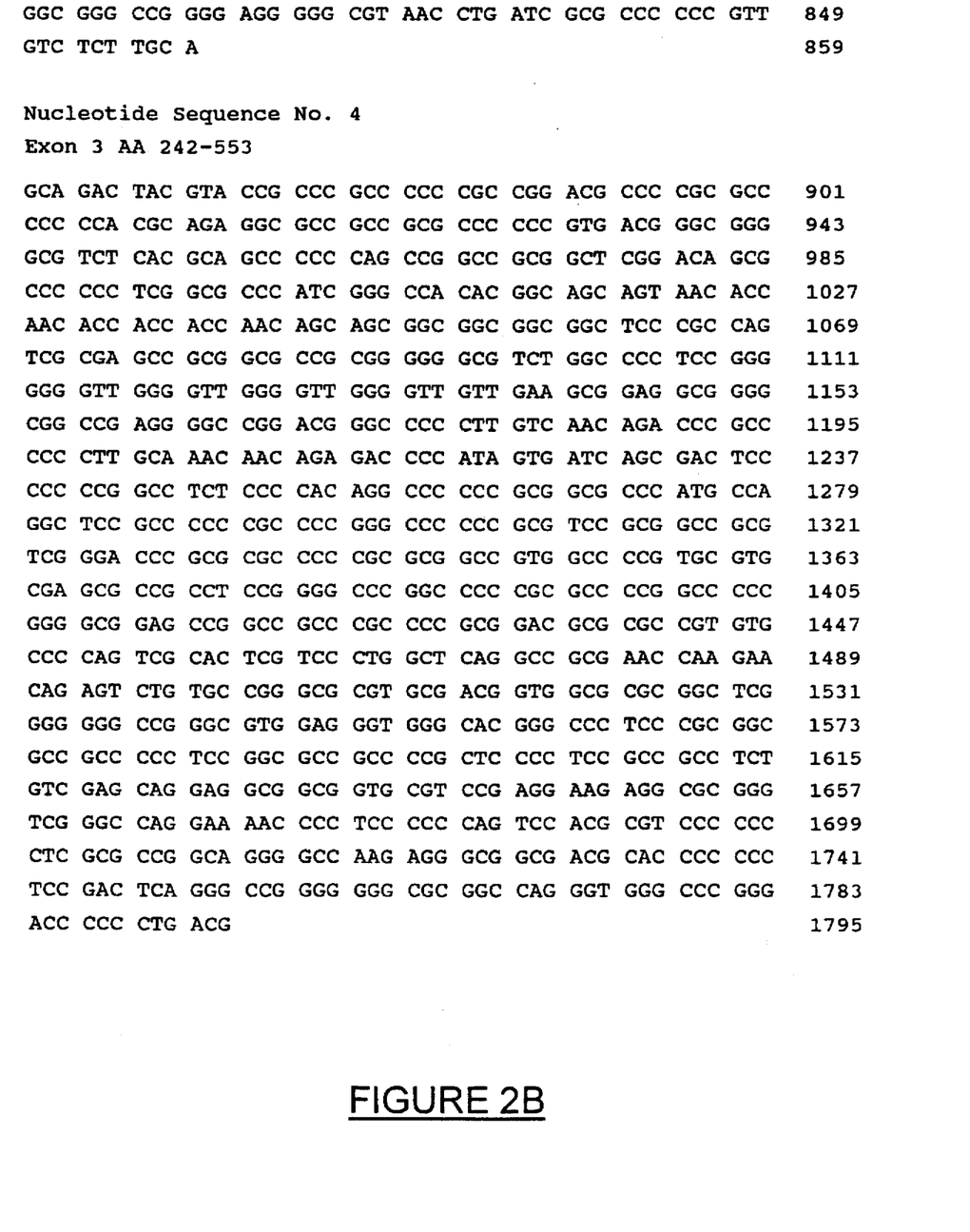

Nucleotide sequences coding for the amino acids, SEQ ID NO: 1–4, which are contained in the mutant proteins are presented in FIG. 2.

EXAMPLE 2

Transactivation Potential of the Dominant Negative Mutants

The pD19T construct was examined for its ability to inhibit a wide variety of HSV-1 promoters, non-HSV-1 promoters, and HSV-1 transactivator proteins in transient expression assays (Table 1 ). In every experiment carded out to date, this plasmid encoding mutant protein has behaved as a powerful repressor of gene activation. The transactivation capabilities of ICP0 as well as another HSV-1 regulatory protein, VP16, were reduced to below basal levels in the presence of the pD16T mutant. Similarly, the high constitutive activity of the SV40 early promoter was abolished when it was cotransfected with pD19T. Identical results were obtained using a third HSV-1 transactivator protein, ICP4, and a second non-HSV-1 promoter, that of the HIV long terminal repeat region. pSG424-ICP0 stimulated gene activation and pHXT had no effect in all of these experiments. Thus, just as the wild type ICP0 protein behaves as a promiscuous transactivator of gene expression in transient assays, the dominant negative mutant of ICP0 in pD19T behaved as a promiscuous repressor.

Cell culture, transfection procedures, and CAT assays. Vero cells were used in all transfection experiments and were grown in minimum essential medium supplemented with 5% calf serum. Transfection of plasmid DNA was performed using calcium phosphate precipitation as described previously, except that the transfected cells were not subjected to glycerol or dimethyl sulfoxide shock, in accordance with the procedure of Everett. Equimolar amounts (approximately 2 µg) of each plasmid were transfected and all concentrations were verified by agarose gel electrophoresis prior to transfection. In most cases, two different cesium chloride gradient-purified plasmid DNA stocks were tested for each construct, and at least two transfections were carried out for each stock. 48 hours after transfection, cells were lysed and extracts prepared by a detergent extraction procedure. Briefly, the cells were washed 3 limes in TM buffer (2 mM $MgCl_2$, 20 mM Tris-HCl, pH 7.5), lysed for 5 min with 0.5 ml lysis buffer (0.1% Triton X-100, 0.25 M Tris-HCl, pH 8.0), scraped into microfuge tubes, and spun for 5 min. The supernatants were heated at 60° C. for 10 min and then spun again for 5 min. 50 ml of each supernatant was used in chloramphenicol acetyltransferase (CAT) assays; the reactions were incubated at 37° C. and included 70 ml Tris-HCl (0.25 M, pH 8.0), 2 ml $^{14}C$-chloramphenicol (NEN-DuPont), and 5 ml n-butyryl coenzyme A (5 mg/ml; Pharmacia). CAT activity was quantitated by a liquid scintillation counting assay. Briefly, each CAT reaction was extracted with 300 ml xylene by vortexing for 30 sec and centrifuging for 3 min. The xylene phase was then back-extracted in a similar fashion using 100 ml Tris-HCl (0.25M, pH 8.0). 200 ml of the final xylene phase, which contains only butyrylated chloramphenicol products, was then added to scintillation fluid and counted.

Various C-terminal truncations of ICP0 are presented in FIG. 3.

The panel of mutant proteins presented in FIG. 3 are different genotypes having the same phenotypic properties as the pD19T mutant. Thus, many other derivatives thereof are possible having similar phenotypic properties and are within the scope of the invention.

The ICP0 proteins are contained in various plasmid constructs of FIG. 3 as follows: pKAT (AA 1–553); pA6T (AA 1–549); pD48T (AA 1–541); pE56T (AA 1–509); pE45T (AA 1–474); pE37T (AA 1–428); pA4T (AA 1–424); pE28T (AA 1–406); pE18T (AA 1–394); pE51T (AA 1–374); pD7T (AA 1–370); pE29T (AA 1–343); pD6T (AA 1–341); pE53T (AA 1–322); priNT (AA 1–312); pE14T (AA 1–290); pE31T (AA 1–278); and pD19T (AA 1–245).

Transactivation potential of carboxy-terminal truncation mutants is represented in FIG. 3.

EXAMPLE 3

Figure 4:
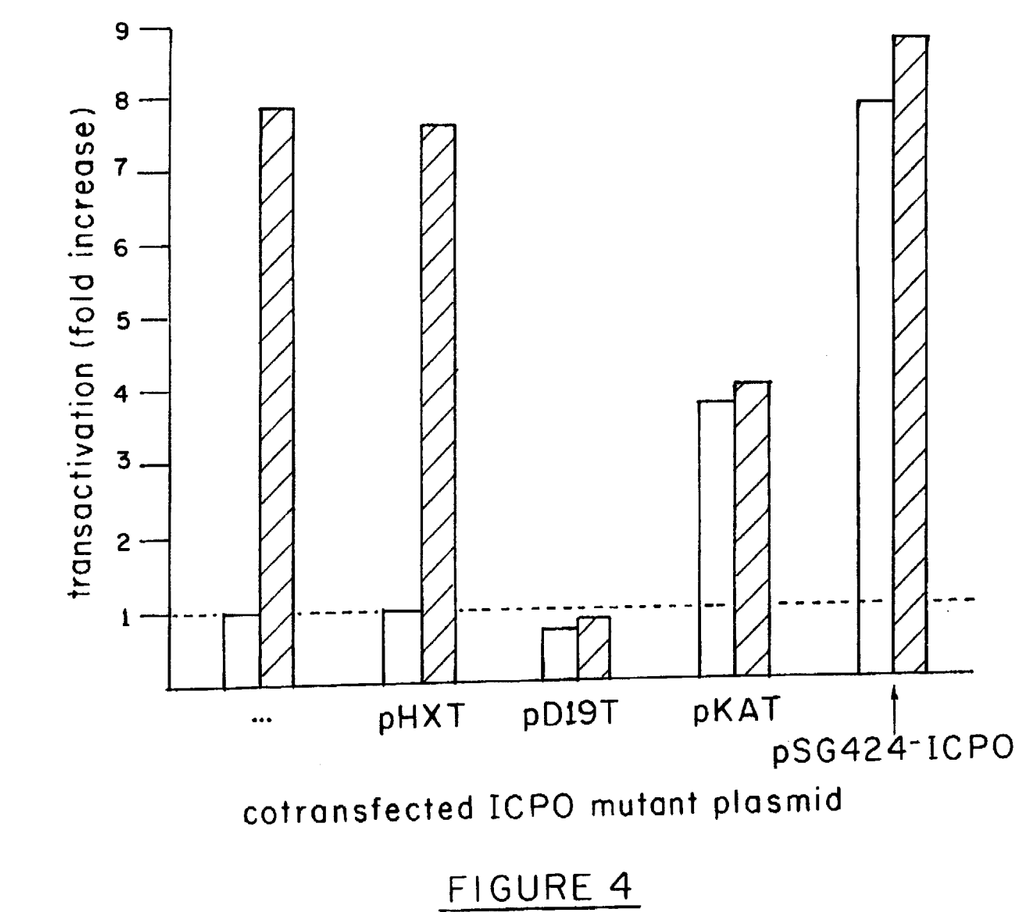
FIG. 4 presents dominant-negative properties of plasmids pD19T and pKAT.

Dominant-Negative Properties of Carboxy-Terminal Truncation Mutants of Plasmid pKAT Dominant-negative properties of carboxy-terminal truncation mutants of plasmid pKAT are presented in FIG. 4. Each of the plasmids indicated at the bottom of the figure was cotransfected with pgC-CAT (open boxes) or with pgC-CAT and the wild-type ICP0 gene in pSG424-ICP0 (black boxes). The ability of each plasmid or combination of plasmids to transactivate the reporter construct is indicated by the increase in CAT activity over that of pgC-CAT transfected alone.

EXAMPLE 4

Promiscuous Repression Mediated by the pDLgT Mutant in Transient Expression Assays Equimolar amounts of plasmid DNAs were transfected into Vero cells, and CAT assays were performed with cellular extracts as described in Example 2. n-Butyryl-[$^{14}C$] chloramphenicol products were extracted from CAT reactions and quantitated by liquid scintillation. Counts were converted to units of CAT enzyme activity by the preparation of a standard curve with purified CAT enzyme (Promega); values represent the total CAT activity in a 60 -mm dish of transfected cells. The results are presented in Table 1.

TABLE 1

Characterization of the pD19T mutant in transient expression assays

| transfected plasmids | CAT enzyme activity (units × $10^{-4}$) |
|---|---|
| effect on transactivation by ICP0: | |
| pgC-CAT | 9.7 |
| pgC-CAT + pHXT | 9.8 |
| pgC-CAT + pSG424-ICP0 | 76.3 |
| pgC-CAT + pD19T | 7.8 |
| pgC-CAT + pSG424-ICP0 + pHXT | 73.9 |
| pgC-CAT + pSG424-ICP0 + pD19T | 8.7 |
| effect on transactivation by VP16: | |
| pTAAT-CAT | 42.2 |
| pTAAT-CAT + pVP16 + pHXT | 213.4 |
| pTAAT-CAT + pVP16 + pSG424-ICP0 | 1,114.1 |
| pTAAT-CAT + pVP16 + pD19T | 24.6 |
| effect on expression of the SV40 early promoter: | |
| pSV40-CAT + pHXT | 115.8 |
| pSV40-CAT + pSG424-ICP0 | 621.5 |
| pSV40-CAT + pD19T | 17.7 |

The strength of the pD19T mutant in repressing the function of its ICP0 parent was compared to that of the prototypic dominant negative mutant of HSV-1, a VP16 derivative which has lost its acidic activation domain [Friedman, A. D., et al., Nature 335:452 (1988)]. These experiments employed pVP16, which encodes all 490 amino acids of the wild type VP16 protein, and pVP16T, which has lost the last 66 amino acids of the wild type protein (FIG. 1). The deletion in the latter plasmid removes the acidic activation domain of VP16 and enables this derivative to function as a dominant negative mutant over the wild type protein. Dilutions of the pD19T and pVP16T mutants were cotransfected with their corresponding wild type plasmids to compare their trans-dominant properties (FIG. 6). VP16 transactivation was reduced to only 25% in the presence of an equimolar concentration of the pVP16T mutant and was restored to greater than 50% in the presence of a 1/5 molar concentration of pVP16T. ICP0 transactivation, however, was reduced to below basal levels in the presence of an equimolar concentration of the pC19T mutant. Moreover, the pD19T mutant had to be diluted to a 1/20 molar concentration for ICP0 transactivation to be restored to greater than 50%. These results indicate that the ICP0 dominant negative mutant is capable of interfering with its wild type protein to a significantly greater extent than the VP16 mutant.

EXAMPLE 5

Characterization of a Plasmid Expressing ICP0R in Transient Expression Assays Equimolar amounts of plasmid DNAs were transfected into Vero cells, except in those experiments which employed the indicated molar dilutions of pD19T plasmid. CAT assays were performed on cellular extracts, and n-butyryl-$^{14}$C-chloramphenicol products were isolated and quantified using liquid scintillation as described in Example 1. Counts were converted to units of CAT activity by the preparation of a standard curve using purified CAT (Promega). Values represent the mean total CAT activity in a 60 mm dish of transfected cells as determined by a minimum of four experiments. The results are presented in Table 2.

TABLE 2

Characterization of the pD19T and pKST mutants in transient expression assays

| transfected plasmids | CAT enzyme activity (units × $10^{-4}$) |
|---|---|
| pgC-CAT | 9.7 |
| pgC-CAT + pHXT | 9.8 |
| pgC-CAT + pSG424-ICP0 | 76.3 |
| pgC-CAT + pD19T | 7.8 |
| pgC-CAT + pKST | 6.0 |
| pgC-CAT + pSG424-ICP0 + pHXT | 73.9 |
| pgC-CAT + pSG424-ICP0 + pKST | 12.6 |
| pgC-CAT + pSG424-ICP0 + pD19T | 8.7 |

EXAMPLE 6

Inhibition of HIV Replication by pD19T

Figure 5:
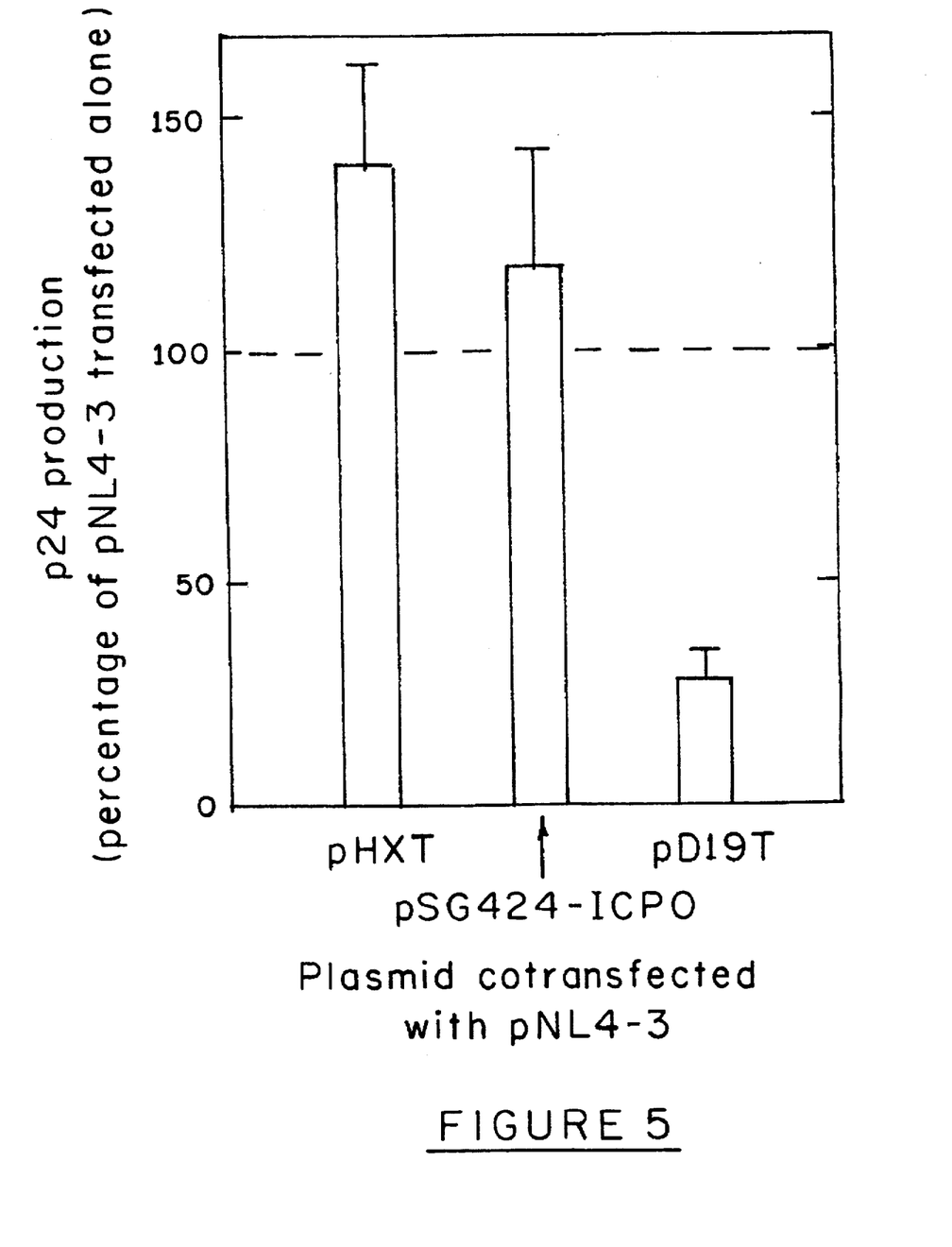
FIG. 5 presents inhibition of HIV replication by pD19T.

Inhibition of HIV replication by pD19T. Quadruplicate cotransfections of 0.2 μg of pNL4-3, which contains a cloned HIV proviral genome (Adachi et al., 1986), with 0.1 μg of the indicated ICP0 plasmid (or with no additional plasmid) were carried out in HeLa cells. The mount of HIV capsid protein p24 in culture supernatants collected from the transfected cells after either 24 or 48 h was then determined. The mean production of p24 protein in those transfections containing ICP0 plasmid DNA is expressed as the percentage of p24 synthesized in the absence of a cotransfected ICP0 plasmid, and represents the compilation of data from both time points. The results are represented in FIG. 5.

Results demonstrate that the pD19T mutant is capable of effectively interfering with virus production during an HSV-1 infection. Since the pD19T mutant was also capable of dramatically repressing the expression of non-HSV-1 genes as well, its potential as a broad spectrum antiviral agent was investigated by examining its effects on a non-HSV-1 viral infection. The previously noted ability of pD19T to inhibit transcription from the HIV LTR indicates that this dominant negative mutant might be an effective therapy in treating HIV infections. To test this possibility, infectious cloned HIV proviral DNA was cotransfected into permissive cell lines with individual ICP0 plasmids. The resulting infections were characterized by determination of the levels of the HIV capsid protein p24. Results indicate that the pD19T mutant was able to significantly inhibit HIV replication in these experiments, since production of p24 antigen was reduced by 75% in the presence of this plasmid (FIG. 5).

EXAMPLE 7

Inhibition of HSV-1 Replication by Dominant Negative Mutants of ICP0 and VP16

The pronounced ability of the pD19T mutant to interfere with promoter activation by three different HSV-1 transactivator proteins suggested that it might manifest antiviral activity if applied in HSV-1 infections. This possibility was tested using a transfection assay approach [Gao, M., et al., J. Virol. 65:2666 (1991)] in which infectious HSV-1 genomic DNA was cotransfected into Vero cells with individual ICP0 or VP16 plasmids. The resulting infections were characterized with respect to plaque formation and total virus yield (Table 3). The pD19T mutant was found to act as a powerful inhibitor of HSV-1 replication in that it nearly abolished plaque formation (3% of the pHXT control) and was the only plasmid which significantly reduced virus yield (11% of the pHXT control). pVP16T and pSG424-ICP0 gave results which paralleled the findings from the transient assay experiments: pVP16T could also inhibit HSV-1 replication (34% of the pHXT control), but was not as effective as pD19T, while pSG424-ICP0 enhanced HSV-1 replication (165% of the pHXT control). Surprisingly, pVP16 caused a modest inhibition in HSV-1 replication (68% of the pHXT control); however, this may be due to the transcriptional squelching abilities or toxic properties of this protein [Sadowski, I., et al., Nature 335:563 (1988); Werstruck, G., et al., J. Virol. 64:984 (1990)].

TABLE 3

Inhibition of HSV-1 replication by dominant negative mutants of ICP0 and VP16

| cotransfected plasmid | plaque count[a] | virus yield[b] |
|---|---|---|
| pHXT | 179 | $2.1 \times 10^6$ |
| pSg424-ICP0 | 296 | $1.1 \times 10^6$ |
| pD19T | 6 | $2.4 \times 10^5$ |
| pVP16 | 121 | $5.1 \times 10^6$ |
| pVP16T | 61 | $3.7 \times 10^6$ |

[a]Duplicate cotransfections of 2 μg of gradient-purified HSV-1 genomic DNA with 2 μg of the indicated plasmid were carried out in Vero cells. The transfected cells were overlaid with medium containing methylcellulose and plaques were counted after 5 days.
[b]Cotransfections were performed as for plaque assays, except that the cells were allowed to grow in normal media until complete cytopathic effect was observed. The resulting supernatants were then tittered to determine the yield of infectious virus per transfection.

HIV Treatment Potential for in vivo Use:

An Example Involving HIV Treatment

Because the pD19T mutant is such a strong suppressor of gene expression, it seems likely that it may have a deleterious effect on the host cell itself. An in vitro system has therefore been devised in which both the antiviral and cytotoxic effects of this protein can be examined. This system can also serve as a useful indicator of the possible utility of the pD 19T mutant as a therapeutic agent in vivo. It features the activation of a latent HIV provirus, the treatment of this induced infection by delivery of the pD19T plasmid, the return of HIV to a state of latency as a result of pD19T-mediated repression, and a long-term assessment of any cytotoxicity by pD 19T following the suppression of HIV replication. Two cell lines have been chosen for initial studies. 8ES/LAV is a CD4+ T cell line and therefore represents the normal target cell for HIV replication; its integrated provirus can be induced by treatment with IUdR. U1/HIV-1 is a promonocyte and may therefore represent the long-term reservoir of HIV in infected individuals; its integrated provirus can be induced by treatment with cytokines or phorbol myristate acetate. After induction of HIV replication and treatment with pD19T, virus replication and antiviral activity can be assessed by the enzymatic assays described above. Moreover, once the induced infection has been reversed in this system, the long-term cytotoxic effects of the pD19T mutant can be examined. Should the protein encoded by pD19T possess not only antiviral but also cytotoxic properties, any number of the recently created variants of pD19T (FIG. 3) can be utilized instead; these derivatives have been found to have modified repression capabilities, which may enable them to suppress HIV replication without harming the host cell.

As more is learned about the potential antiviral activity of pD19T through the cell culture studies described above, the focus of this project will shift to the development of this repressor protein for possible in vivo use. The goal in treating replicating HIV in infected individuals using the pD19T mutant would be similar to that outlined above for cell culture systems: an active HIV infection would be driven back into a latent state by the action of a powerful repressor protein. Thereafter, each recurring induction event would be suppressed by additional treatment with pD19T as needed. Successful application of this strategy could therefore significantly prolong the lifetime of an infected individual. Since the pD19T mutant may be toxic to the host cell, a successful antiviral therapy would have to ensure that the repressor gene enters only cells susceptible to HIV, that it is expressed only in cells which contain an actively replicating virus, and that it fails to be expressed once it has forced the HIV infection back into a latent state. Numerous methods of viral- and nonviral- mediated tissue-specific gene delivery have been developed [Felgner, P. L., et al., Nature 349:351 (1991); Geller, A. I., et al., Science 241:1667 (1988); Mann, R., et al., Cell 33:153 (1983)] which would make it possible to direct pD19T into a limited set of cells. Moreover, the repressor gene could be packaged and delivered exclusively to CD4+ T cells using a defective HIV strain as a vector. The pD19T mutant can also be engineered so that it is expressed by an intrinsically weak promoter which contains a copy of the tat-responsive element. As a result, the repressor protein should be produced only in cells which contain an active HIV infection with high levels of tat protein. As the infection subsides and the concentration of tat protein diminishes, the expression of the repressor gene will cease and any cytotoxic effects on the host cell will be minimized. By this combination of approaches, the powerful but nonspecific repression activity of the pD19T mutant may be specifically and exclusively directed against HIV replication.

Although the potential antiviral properties of pD19T have been emphasized in this work, numerous other important uses of this mutant can be imagined. Its repression functions could be directed against cancer cells as an antitumor agent. It could be employed as the gene of choice for suppressing gene expression or virus replication in specific tissues of transgenic mice. Finally, additional studies with pD19T will almost certainly help to unravel the unknown mechanism by which ICP0 activates gene expression. In several mutational analyses, ICP0 function has been shown to be highly sensitive to disruptions in the coding sequence of the second exon [Everett, R. D., et al., EMBO J. 6:2069 (1987); Everett, R. D., et al., J. Mol. Biol. 202:87 (1988); Cai, W., et al., J. Virol. 63:4579 (1989); Chen, J. et al., Virology 180:207 (1991)]. The dominant negative mutant of ICP0 in pD 19T is encoded almost entirely by this same region. Thus, the second exon probably encodes a critical domain that interacts with the unknown cellular protein through which ICP0 mediates its activation and the pD19T mutant mediates its repression. Further studies with this domain encoded by pD19T may facilitate the identification and purification of this cellular target.

Thus, while I have illustrated and described the preferred embodiment of my invention, it is to be understood that this invention is capable of variation and modification, and I, therefore, do not wish or intend to be limited to the precise terms set forth, but desire and intend to avail myself of such changes and alterations which may be made for adapting the invention of the present invention to various usages and conditions. Accordingly, such changes and alterations are properly intended to be within the full range of equivalents and, therefore, within the purview of the following claims.

The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described my invention and the manner and process of making and using it in such full, clear, concise, and exact terms so as to enable any person skilled in the art to which it pertains, or with which it is most nearly connected, to make and use the same.

What is claimed is:

1. A nucleotide sequence coding for a novel protein ICPOR which protein contains all 241 amino acids by exons 1 and 2 of the gene encoding ICPO, plus an additional 21 amino acids derived from translation of the unspliced second intron.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 57 bases
        ( B ) TYPE: nucleic acid
        ( C ) STRANDEDNESS: both
        ( D ) TOPOLOGY: linear     ( i i ) MOLECULE TYPE: genomic DNA     ( x ) PUBLICATION INFORMATION:
        ( A ) AUTHORS: Perry, L.J.; Rixon, F.J.; Everett, R.D.; Frame,
            M.C.; McGeoch, D.J.
        ( B ) TITLE: Characterization of the IE110 Gene of Herpes
            Simplex Virus Type 1
        ( C ) JOURNAL: J. gen. Virol.
        ( D ) VOLUME: 67
        ( F ) PAGES: 2365-2380
        ( G ) DATE: 1986
        ( K ) RELEVANT RESIDUES IN SEQ ID NO:1- 4: ALL     ( x i ) SEQUENCE DESCRIPTION: SEQ ID NO:1:

```
ATG GAG CCC CGC CCC GGA GCG AGT ACC CGC CGG CCT GAG GGC    42

CGC CCC CAG CGC GAG         57
```

( 2 ) INFORMATION FOR SEQ ID NO:2:

( i ) SEQUENCE CHARACTERISTICS:
        ( A ) LENGTH: 666 bases
        ( B ) TYPE: nucleic acid
        ( C ) STRANDEDNESS: both
        ( D ) TOPOLOGY: linear     ( i i ) MOLECULE TYPE: genomic DNA     ( x i ) SEQUENCE DESCRIPTION: SEQ ID NO:2:

```
CCC GCC CCG GAT GTC TGG GTG TTT CCC TGC GAC CGA GAC CTG    42

CCG GAC AGC AGC GAC TCT GAG GCG GAG ACC GAA GTG GGG GGG    84

CGG GGG GAC GCC GAC CAC CAT GAC GAC GAC TCC GCC TCC GAG    126

GCG GAC AGC ACG GAC ACG GAA CTG TTC GAG ACG GGG CTG CTG    168

GGG CCG CAG GGC GTG GAT GGG GGG GCG GTC TCG GGG GGG AGC    210

CCC CCC CGC GAG GAA GAC CCC GGC AGT TGC GGG GGC GCC CCC    252

CCT CGA GAG GAC GGG GGG AGC GAC GAG GGC GAC GTG TGC GCC    294

GTG TGC ACG GAT GAG ATC GCG CCC CAC CTG CGC TGC GAC ACC    336

TTC CCG TGC ATG CAC CGC TTC TGC ATC CCG TGC ATG AAA ACC    378

TGG ATG CAA TTG CGC AAC ACC TGC CCG CTG TGC AAC GCC AAG    420

CTG GTG TAC CTG ATA GTG GGC GTG ACG CCC AGC GGG TCG TTC    462
```

```
AGC ACC ATC CCG ATC GTG AAC GAC CCC CAG ACC CGC ATG GAG      504

GCC GAG GAG GCC GTC AGG GCG GGC ACG GCC GTG GAC TTT ATC      546

TGG ACG GGC AAT CAG CGG TTC GCC CCG CGG TAC CTG ACC CTG      588

GGG GGG CAC ACG GTG AGG GCC CTG TCG CCC ACC CAC CCG GAG      630

CCC ACC ACG GAC GAG GAT GAC GAC GAC CTG GAC GAC              666
```

( 2 ) INFORMATION FOR SEQ ID NO:3:

( i ) SEQUENCE CHARACTERISTICS:
        ( A ) LENGTH: 136 bases
        ( B ) TYPE: nucleic acid
        ( C ) STRANDEDNESS: both
        ( D ) TOPOLOGY: linear     ( i i ) MOLECULE TYPE: genomic DNA     ( x i ) SEQUENCE DESCRIPTION: SEQ ID NO:3:

```
GGT GAG GCG GGG GGC GGC AAG GAC CCT GGG GGA GGA GGA GGA       42

GGA GGG GGG GGG AGG GAG GAA TAG GCG GGC GGG CGA GGA AAG       84

GGC GGG CCG GGG AGG GGG CGT AAC CTG ATC GCG CCC CCC GTT      126

GTC TCT TGC A                                                136
```

( 2 ) INFORMATION FOR SEQ ID NO:4:

( i ) SEQUENCE CHARACTERISTICS:
        ( A ) LENGTH: 936 bases
        ( B ) TYPE: nucleic acid
        ( C ) STRANDEDNESS: both
        ( D ) TOPOLOGY: linear     ( i i ) MOLECULE TYPE: genomic DNA     ( x i ) SEQUENCE DESCRIPTION: SEQ ID NO:4:

```
GCA GAC TAC GTA CCG CCC GCC CCC CGC CGG ACG CCC CGC GCC       42

CCC CCA CGC AGA GGC GCC GCC GCG CCC CCC GTG ACG GGC GGG       84

GCG TCT CAC GCA GCC CCC CAG CCG GCC GCG GCT CGG ACA GCG      126

CCC CCC TCG GCG CCC ATC GGG CCA CAC GGC AGC AGT AAC ACC      168

AAC ACC ACC ACC AAC AGC AGC GGC GGC GGC TCC CGC CAG          210

TCG CGA GCC GCG GCG CCG CGG GGG GCG TCT GGC CCC TCC GGG      252

GGG GTT GGG GTT GGG GTT GGG GTT GTT GAA GCG GAG GCG GGG      294

CGG CCG AGG GGC CGG ACG GGC CCC CTT GTC AAC AGA CCC GCC      336

CCC CTT GCA AAC AAC AGA GAC CCC ATA GTG ATC AGC GAC TCC      378

CCC CCG GCC TCT CCC CAC AGG CCC CCC GCG GCG CCC ATG CCA      420

GGC TCC GCC CCC CGC CCC GGG CCC CCC GCG TCC GCG GCC GCG      462

TCG GGA CCC GCG CGC CCC CGC GCG GCC GTG GCC CCG TGC GTG      504

CGA GCG CCG CCT CCG GGG CCC GGC CCC CGC GCC CCG GCC CCC      546

GGG GCG GAG CCG GCC GCC CGC CCC GCG GAC GCG CGC CGT GTG      588

CCC CAG TCG CAC TCG TCC CTG GCT CAG GCC GCG AAC CAA GAA      630

CAG AGT CTG TGC CGG GCG CGT GCG ACG GTG GCG CGC GGC TCG      672

GGG GGG CCG GGC GTG GAG GGT GGG CAC GGG CCC TCC CGC GGC      714

GCC GCC CCC TCC GGC GCC GCC CCG CTC CCC TCC GCC GCC TCT      756
```

-continued

```
GTC GAG CAG GAG GCG GCG GTG CGT CCG AGG AAG AGG CGC GGG    798

TCG GGC CAG GAA AAC CCC TCC CCC CAG TCC ACG CGT CCC CCC    840

CTC GCG CCG GCA GGG GCC AAG AGG GCG GCG ACG CAC CCC CCC    882

TCC GAC TCA GGG CCG GGG GGG CGC GGC CAG GGT GGG CCC GGG    924

ACC CCC CTG ACG                                            936
```

( 2 ) INFORMATION FOR SEQ ID NO:5:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear     ( i i ) MOLECULE TYPE: nucleic acid
        ( A ) DESCRIPTION: DNA equivalent of ICPO mRNA
            transcript     ( i i i ) HYPOTHETICAL: no     ( i v ) ANTI-SENSE: no     ( x i ) SEQUENCE DESCRIPTION: SEQ ID NO:5:

```
CCCCCCGTTG TCTCTTGCAG CAGACTACGT ACCGCCCG                   38
```

( 2 ) INFORMATION FOR SEQ ID NO:6:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear     ( i i ) MOLECULE TYPE: nucleic acid
        ( A ) DESCRIPTION: DNA encoding the anti-sense
            oligonucleotide to the ICPO mRNA transcript     ( i i i ) HYPOTHETICAL: no     ( i v ) ANTI-SENSE: yes     ( x i ) SEQUENCE DESCRIPTION: SEQ ID NO:6:

```
TACGTAGTCT GCTGCAAGAG ACAA                                  24
```